US010980975B2

(12) United States Patent  
Horvitz

(10) Patent No.: US 10,980,975 B2  
(45) Date of Patent: Apr. 20, 2021

(54) SYSTEM, DEVICE AND METHOD FOR ADVANCING AN ARTICLE ALONG A PATH

(71) Applicant: IBEX TECHNOLOGIES LTD., Beer-Sheva (IL)

(72) Inventor: Amir Horvitz, D.N. Hanegev (IL)

(73) Assignee: IBEX TECHNOLOGIES LTD., Beer-Sheva (IL)

( * ) Notice: Subject to any disclaimer, the term of this patent is extended or adjusted under 35 U.S.C. 154(b) by 284 days.

(21) Appl. No.: 16/302,910

(22) PCT Filed: May 17, 2017

(86) PCT No.: PCT/IL2017/050555  
§ 371 (c)(1),  
(2) Date: Nov. 19, 2018

(87) PCT Pub. No.: WO2017/199256  
PCT Pub. Date: Nov. 23, 2017

(65) Prior Publication Data  
US 2019/0184137 A1 Jun. 20, 2019

Related U.S. Application Data

(60) Provisional application No. 62/338,536, filed on May 19, 2016.

(51) Int. Cl.  
*A61M 25/01* (2006.01)  
*A61B 1/00* (2006.01)  
(Continued)

(52) U.S. Cl.  
CPC ....... *A61M 25/0119* (2013.01); *A61B 1/0011* (2013.01); *A61B 1/00151* (2013.01);  
(Continued)

(58) Field of Classification Search  
CPC .......... A61M 25/0119; A61M 25/0043; A61M 25/0662; A61M 2025/0681; A61B 1/0011; A61B 1/00151  
See application file for complete search history.

(56) References Cited

U.S. PATENT DOCUMENTS 3,168,092 A * 2/1965 Silverman .............. A61B 46/13  
                                                                       600/7  
4,043,345 A     8/1977 Kramann et al.  
(Continued)

FOREIGN PATENT DOCUMENTS

CN       1293550 A     5/2001  
CN     102905608 A     1/2013  
WO   2010/020985 A1     2/2010

*Primary Examiner* — Bhisma Mehta  
*Assistant Examiner* — James D Ponton  
(74) *Attorney, Agent, or Firm* — Vorys, Sater, Seymour and Pease LLP; Anthony P. Venturino

(57) ABSTRACT

Provided is a system for advancing an article along a path. The system may include a head member; a dispatching member, and an eversion sleeve configured with an inverted portion having a sleeve end configured to be fixed to the dispatching member. The system may also include an everting portion configured for articulating to the head member and an un-inverted portion configured to extend from the everting portion towards the dispatching member, at least partially within the inverted portion.

20 Claims, 13 Drawing Sheets

(51) Int. Cl.
*A61M 25/00* (2006.01)
*A61M 25/06* (2006.01)

(52) U.S. Cl.
CPC .... *A61M 25/0043* (2013.01); *A61M 25/0662* (2013.01); *A61M 2025/0681* (2013.01)

(56) References Cited

U.S. PATENT DOCUMENTS

| | | | |
|---|---|---|---|
| 4,077,610 | A | 3/1978 | Masuda |
| 4,493,711 | A | 1/1985 | Chin et al. |
| 5,259,364 | A | 11/1993 | Bob et al. |
| 6,554,793 | B1 * | 4/2003 | Pauker ............... A61B 1/00151 604/158 |
| 2001/0044595 | A1 | 11/2001 | Reydel et al. |
| 2003/0105386 | A1 | 6/2003 | Voloshin et al. |
| 2003/0208223 | A1 | 11/2003 | Kleiner |
| 2007/0203472 | A1 | 8/2007 | Nachmani |
| 2011/0009943 | A1 | 1/2011 | Paul et al. |
| 2011/0139665 | A1 | 6/2011 | Madsen |
| 2013/0035749 | A1 | 2/2013 | Farag |

* cited by examiner

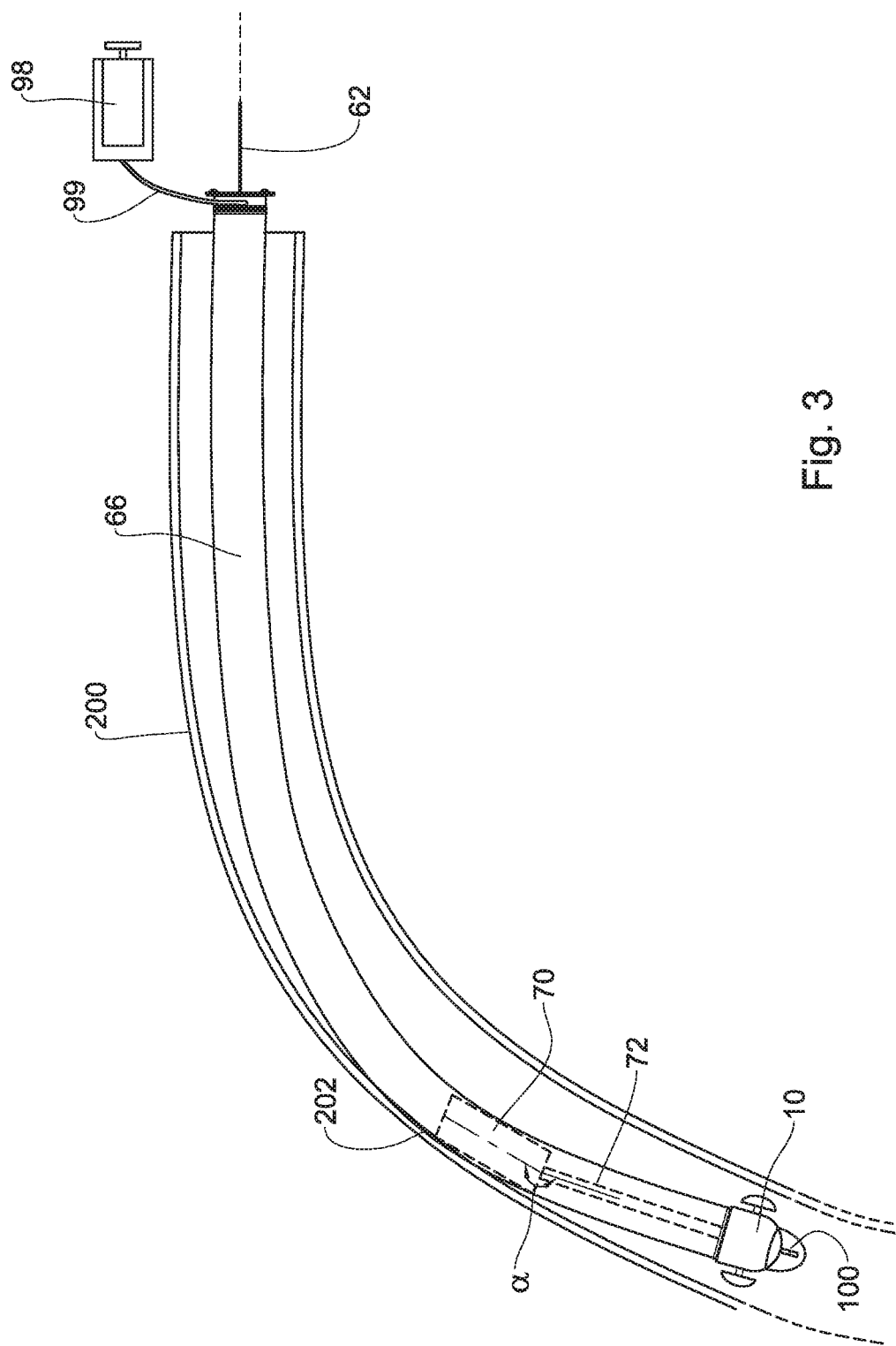

SYSTEM, DEVICE AND METHOD FOR ADVANCING AN ARTICLE ALONG A PATH

TECHNICAL FIELD

This presently disclosed subject matter relates to the field of systems and methods for advancing an article along a path.

BACKGROUND

The principle of an eversion sleeve to be used in conjunction with a catheter has known for many years in the field of medical devices. Such sleeves are used for enabling an access to different body cavities such as the colon system or the urethral system, and navigating within respective biological lumens. Below are a number of prior art examples in which a device having an eversion sleeve is used.

U.S. Pat. No. 4,493,711 discloses a catheter having an inverted-evertable non-elastic tube with a diameter throughout equal to or greater than the catheter body, an axially aligned end opening at the distal end, and a multifold configuration of the distal end to maintain end-sealing during inversion and eversion.

US 2003/208223 discloses an apparatus incorporating an elongate hollow element for being positioned along a body cavity of a patient. The hollow element has a leading region and a trailing region and is arranged for being progressively everted along the hollow element from the leading region to thereby be increasingly extended for progressively lining the body cavity as the trailing region follows along.

U.S. Pat. No. 4,043,345 discloses a catheter including a flexible hose attached to one end of a rigid tube through which fluid pressure may be applied to invert said hose from an invaginated position within said tube to an exserted position extending outwardly of said tube having formed at the distal end of said hose a valve which remains closed when the hose is in the invaginated position and which opens with the hose in its exserted position.

SUMMARY OF THE PRESENTLY DISCLOSED SUBJECT MATTER

According to a first aspect of the presently disclosed subject matter, there is provided a system for advancing an article along a path, comprising:
  a head member;
  a dispatching member; and
  an eversion sleeve configured with an inverted portion having a sleeve end configured to be fixed to the dispatching member, an everting portion configured for articulating to the head member and an un-inverted portion configured to extend from the everting portion towards the dispatching member, at least partially within the inverted portion; said un-inverted portion and said inverted portion are configured to form a fluid receiving space therebetween for receiving a propelling fluid for exerting force on the everting portion, thereby gradually advancing a segment of the un-inverted non-inverted portion towards the head member, causing it to displace with respect to the head member, gradually advancing a respective segment of the everting portion into the inverted portion, thereby everting said eversion sleeve inside out and advancing the head member along the path;
  wherein said head member is configured with one or more revolving elements configured for engaging said everting portion and for revolving upon displacement of the everting portion thereon with respect to the head member.

According to a second aspect of the presently disclosed subject matter, there is provided a device for advancing an article along a path, comprising:
  a head member;
  a dispatching member;
  an eversion sleeve configured with an inverted portion having a sleeve end fixed to the dispatching member, an everting portion articulated to the head member and a non-inverted portion extending from the everting portion towards the dispatching member, at least partially within the inverted portion; and
  a space formed between said non-inverted portion and said inverted portion for receiving a propelling fluid for exerting force on the everting portion, thereby gradually advancing a segment of the non-inverted portion towards the head member causing it to displace with respect to the head member and gradually advancing a respective segment of the everting portion into the inverted portion, thereby everting said eversion sleeve inside out and advancing the head member along the path;
  wherein said head member is configured with one or more revolving elements configured for engaging said everting portion and for revolving upon displacement of the everting portion thereon with respect to the head member.

The term 'article' as used herein in the specification and claims, denotes the head member with or without an electric or mechanical unit mounted thereto, a video camera, a stills camera, an imaging system, sensing system, a treatment system, a working tool, a communication system, a treatment equipment, etc.

The term 'path' as used herein in the specification and claims, denotes a canal, a channel, a cavity, a tunnel, an underpass, a lumenway, a tube, a lumen, a conduit, etc.

The term 'fluid' as used herein in the specification and claims, denotes a gaseous fluid, such as air, helium, etc. or a liquid fluid such as water, oil, etc.

The eversion sleeve of the presently disclosed subject matter is made of a resilient and/or flexible material that allows advancing the eversion sleeve with the head member mounted thereto along a curved path with the ability to curve and bend the eversion sleeve during the advancement when contacting the walls of the path, thereby following the path. During advancement of the eversion sleeve, it will follow a path of least resistance, so when a bend occurs, the eversion sleeve will follow it.

The eversion process involves deployment of the eversion sleeve by turning it inside out. This allows advancing the eversion sleeve and its head member with a substantially low friction within the internal surface of the path that can be rough and can include various obstacles therealong, thereby allowing easy and reliable self-propulsion of the head member along the path. Eventually, the eversion process is such that the inverted portion of the sleeve remains substantially stationary with respect to the walls of the path, and the main element that may be subject to friction with the path is the head member.

The revolving elements facilitate the displacement of the everting portion with respect to the head member by allowing the everting portion to roll on the revolving elements, instead of sliding on an internal portion or any other member of the head member, if provided without the revolving elements. The revolving elements reduce friction between the eversion sleeve and the head member by about 90%. This means that if the head member is provided without the revolving elements, and the everting portion is configured for slidingly displacing therein, the friction coefficient at the engagement area therebetween is X. However, if the head member is configured with revolving elements as provided by the presently disclosed subject matter, the friction coefficient can be reduced even to about 0.1X. The revolving elements thus reduce the resistance of the head member to the displacement of the eversion sleeve with respect thereto, and allow increasing the length of the inverted portion of the eversion sleeve to a greater extent per given force exerted on the everting portion.

According to a third aspect of the presently disclosed subject matter, there is provided a method for assembling a system for advancing an article along a path, the system comprising: a head member configured with one or more revolving elements configured for engaging said everting portion and for revolving upon displacement of the everting portion thereon with respect to the head member; a dispatching member having a nozzle; and an eversion sleeve; the method comprising:

(i) introducing a part of said eversion sleeve via said nozzle;

(ii) everting the eversion sleeve inside out, thereby forming an inverted portion having a sleeve end, an everting portion and a non-inverted portion extending from the everting portion towards the dispatching member, at least partially within the inverted portion; and (iii) mounting said everting portion to said head member so that said revolving elements are engaging an external surface of said everting portion to facilitate its to displace with respect to the head member; and (iv) sealingly fixing said sleeve end to said dispatching member, thereby forming a space therebetween for receiving a propelling fluid for exerting force on the everting portion.

The method for assembling can further include a step of introducing said part of said eversion sleeve via a retaining member, which is performed between steps (i) and (ii), and a step of locating the retaining member at an internal surface of the everting portion for applying an outwardly pressing force thereon, which is performed between steps (iii) and (iv).

The step (iv) can further include a step of locating the retaining member within a wide portion of the head member.

According to a fourth aspect of the presently disclosed subject matter, there is provided a method for using a device for advancing an article along a path, comprising:

(i) providing the device, comprising: a head member; a dispatching member; an eversion sleeve configured with an inverted portion having a sleeve end fixed to the dispatching member, an everting portion articulated to the head member and a non-inverted portion extending from the everting portion towards the dispatching member, at least partially within the inverted portion; and a space formed between said non-inverted portion and said inverted portion; said head member being configured with one or more revolving elements configured for engaging said everting portion and for revolving upon displacement of the everting portion thereon with respect to the head member;

(ii) locating said device at a particular location at the path with the head member facing towards an advancement direction along the path; and (iii) introducing a propelling fluid into the space for exerting force on the everting portion, thereby gradually advancing a segment of the non-inverted portion towards the head member causing it to displace with respect to the head member while the revolving elements are revolving and gradually advancing a respective segment of the everting portion into the inverted portion, thereby everting said eversion sleeve inside out and advancing the head member along the advancement direction.

The method can further comprise steps of: providing the device with a steering mechanism having a body member connected to a front end of the head member; and operating the steering mechanism for directing the advancement direction of the head member.

Any one or more of the following features, designs and configurations can be incorporated in the presently disclosed subject matter according to the first, second, third and fourth aspects, independently or in combination thereof.

The head member can be configured with an internal portion for retaining the everting portion and facilitating the everting portion to advance with respect to the head member.

The revolving elements can comprise one or more first revolving elements configured with said internal portion for engaging an external surface of said everting portion.

The head member can be made of a substantially rigid material that preserves its shape also when the force exerted by the propelling fluid on the everting portion is reduced or terminated (i.e., the pressure of the propelling fluid within the space drops). This can allow the head member and/or the entire device to perform its designated function at any location along the path also when there is a pressure drop of propelling fluid.

The internal portion of the head member can be configured with at least one narrow portion having a first cross-sectional diameter D1 taken perpendicularly to its length and at least one wide portion having a second cross-sectional diameter D2 taken perpendicularly to its length, which is greater than D1. The at least one narrow portion is configured to engage the external surface of the everting portion and prevent axial displacement of the head member with respect to the everting portion, while allowing the everting portion to displace with respect to the internal portion.

The first revolving elements can be disposed at said narrow portion.

The first revolving elements can define the first cross-sectional diameter D1.

The narrow portion can be formed as a circumferential groove formed in the head member.

The at least one narrow portion can be disposed closer to the inverted portion than the at least one wide portion.

The at least one narrow portion can be disposed between two of said wide portions.

The head member can further comprise a retaining member configured for engaging an internal surface of the everting portion on which the force of the propelling fluid is to be exerted, and applying an outwardly pressing force thereon, thereby retaining the everting portion while allowing the everting portion for displacing with respect to the internal portion.

The revolving elements can comprise one or more second revolving elements configured with the retaining member for engaging the internal surface of the everting portion and for revolving upon displacement of the everting portion thereon with respect to the head member.

The first revolving elements and/or the second revolving elements can be any one of: rollers, wheels, balls.

The first revolving elements can be equally spaced from each other.

The second revolving elements can be equally spaced from each other.

One or more of the first revolving elements can be disposed in proximity to one or more of the second revolving elements so that the everting portion is disposed therebetween.

The retaining member can be configured as a first retaining sub-member and a second retaining sub-member disposed consecutively along the length of the head member.

The first retaining sub-member and the second retaining sub-member can be connected to each other.

Each one of the first retaining sub-member and the second retaining sub-member can be configured with said second revolving elements.

The first retaining sub-member and the second retaining sub-member can be spaced from each so that the narrow portion is disposed at the space therebetween.

The retaining member can be located in close proximity to the wide portion of the internal portion. The retaining member can have an exterior face having a shape which is mimicking the shape of the wide portion.

The retaining member can have a central opening for allowing the non-inverted portion to pass therethrough.

The retaining member can have a torus shape.

The head member can further be configured with a frontal portion with a rounded profile. The rounded profile can be a sphere-like profile.

The dispatching member can have an annular shape and can be configured with a perimetric rim for sealingly circumferentially fixing to the sleeve end, a nozzle for allowing the internal portion to pass therethorugh, and an inlet for interfacing with a pumping mechanism configured for introducing the propelling fluid into the space.

The dispatching member can be configured with a nozzle disposed at its center.

The system and the device can comprise a pumping mechanism for introducing the propelling fluid into the space, thereby generating a positive pressure therein and exerting the force on the everting portion.

The eversion sleeve can be made of one of the following materials: silk, nylon, rubber, deformable plastic material.

The eversion sleeve can be made of a fluid-tight material.

The space can be sealed from the surroundings.

The interior of the internal portion can define an elongate lumen allowing electrically or mechanically communicating therethrough between an exterior of the device at the surroundings of the dispatching member and the head member and its surrounding. The elongate lumen can allow introducing therethrough objects (e.g., endoscopes, measuring instruments, sensors, working tools), cables (e.g., electric cables, Bowden cables, fibers), or tubes.

The head member can be mounted to an operational unit including one or more of the following: a video camera, a stills camera, an imaging system, sensing system, a treatment system, a working tool, and a communication system.

The head member and the operational unit can be integrated into a single unit.

According to a fifth aspect of the presently disclosed subject matter, there is provided a system for advancing an article along a path, comprising:

a head member;

a dispatching member;

an eversion sleeve configured with an inverted portion having a sleeve end configured to be fixed to the dispatching member, an everting portion configured for articulating to the head member and an un-inverted portion configured to extend from the everting portion towards the dispatching member, at least partially within the inverted portion; said un-inverted portion and said inverted portion are configured to form a fluid receiving space therebetween for receiving a propelling fluid for exerting force on the everting portion, thereby gradually advancing a segment of the un-inverted non-inverted portion towards the head member, causing it to displace with respect to the head member, gradually advancing a respective segment of the everting portion into the inverted portion, thereby everting said eversion sleeve inside out and advancing the head member along the path; and a steering mechanism configured to be mounted on the head member for directing the head member during its advancement along the path.

According to a sixth aspect of the presently disclosed subject matter, there is provided a device for advancing an article along a path, comprising:

a head member;

a dispatching member;

an eversion sleeve configured with an inverted portion having a sleeve end fixed to the dispatching member, an everting portion articulated to the head member and a non-inverted portion extending from the everting portion towards the dispatching member, at least partially within the inverted portion;

a space formed between said non-inverted portion and said inverted portion for receiving a propelling fluid for exerting force on the everting portion, thereby gradually advancing a segment of the non-inverted portion towards the head member causing it to displace with respect to the head member and gradually advancing a respective segment of the everting portion into the inverted portion, thereby everting said eversion sleeve inside out and advancing the head member along the path; and a steering mechanism mounted to the head member for directing the head member during its advancement along the path.

Any one or more of the following features, designs and configurations can be incorporated in the presently disclosed subject matter according to the fifth and sixth aspects, independently or in combination thereof.

The steering mechanism can comprise at least one pair of wheels connected to the head member at two opposite sides thereof. Each of the wheels can be connected to the head member with its respective axle. The axle can extend from an external surface of the head member.

The head member can further comprise a retaining member configured for engaging an internal surface of the everting portion on which the force of the propelling fluid is to be exerted, and applying an outwardly pressing force thereon, thereby retaining the everting portion in proximity to the internal portion while allowing the everting portion for displacing with respect to the internal portion.

The steering mechanism can further comprise a controlling mechanism configured for controlling the direction of said pair of wheels.

The controlling mechanism can be attached to the retaining member for directing movement of the head member with respect to a longitudinal axis of the eversion sleeve.

The controlling mechanism can comprise a sleeve supporting member connected to the retaining member and extending within said inverted portion and engaging an internal surface of said inverted portion. The sleeve supporting member can be pivotally connected to the retaining member. The sleeve supporting member can be configured to preserve the shape of said inverted portion at the engagement area therebetween.

The controlling mechanism can further comprise an angle-regulating mechanism configured for regulating the angle between the retaining member and the sleeve supporting member on at least one plane.

The angle-regulating mechanism can be configured for regulating the angle between the retaining member and the sleeve supporting member on two perpendicular planes. The angle-regulating mechanism can comprise a hydraulic cylinder.

The sleeve supporting member can be connected to the retaining member via an extension member. The sleeve supporting member can be pivotally connected to the extension member, thereby providing the pivotal connection of the sleeve supporting member to the retaining member.

The controlling mechanism can further comprise a sub-supporting member pivotally connected at one end thereof to the retaining member, and at another end thereof pivotally connected to the sleeve supporting member. The sub-supporting member can be pivotally connected at said one end thereof to the extension member.

The angle-regulating mechanism can be configured for regulating two angles: a first angle between the extension member and the sub-supporting member, and a second angle between the sleeve supporting member and the sub-supporting member. The first angle and the second angle can be disposed at two perpendicular planes. The angle-regulating mechanism can comprise at least one hydraulic cylinder.

The extension member, the sleeve supporting member and the sub-supporting member can be configured with an internal opening extending therethrough for allowing said non-inverted portion to pass therethrough.

According to a seventh aspect of the presently disclosed subject matter, there is provided a system for advancing an article along a path, comprising:

a head member;

a dispatching member;

an eversion sleeve configured with an inverted portion having a sleeve end configured to be fixed to the dispatching member, an everting portion configured for articulating to the head member and a non-inverted portion configured to extend from the everting portion towards the dispatching member, said non-inverted portion and said inverted portion are configured to form a space therebetween for receiving a propelling fluid for exerting force on the everting portion, thereby gradually advancing a segment of the non-inverted portion towards the head member causing it to displace with respect to the head member and gradually advancing a respective segment of the everting portion into the inverted portion, thereby everting said eversion sleeve inside out and advancing the head member along the path;

a retaining member configured for engaging an internal surface of the everting portion on which the force of the propelling fluid is to be exerted, and applying an outwardly pressing force thereon, thereby retaining the everting portion in proximity to the internal portion while allowing the everting portion for displacing with respect to the internal portion; and a sleeve supporting member connected to the retaining member and extending within said inverted portion and engaging an internal surface of said inverted portion.

According to an eighth aspect of the presently disclosed subject matter, there is provided a device for advancing an article along a path, comprising:

a head member;

a dispatching member;

an eversion sleeve configured with an inverted portion having a sleeve end fixed to the dispatching member, an everting portion articulated to the head member and a non-inverted portion extending from the everting portion towards the dispatching member, at least partially within the inverted portion;

a space formed between said non-inverted portion and said inverted portion for receiving a propelling fluid for exerting force on the everting portion, thereby gradually advancing a segment of the non-inverted portion towards the head member causing it to displace with respect to the head member and gradually advancing a respective segment of the everting portion into the inverted portion, thereby everting said eversion sleeve inside out and advancing the head member along the path;

a retaining member engaging an internal surface of the everting portion on which the force of the propelling fluid is to be exerted, and applying an outwardly pressing force thereon, thereby retaining the everting portion in proximity to the internal portion while allowing the everting portion for displacing with respect to the internal portion; and a sleeve supporting member connected to the retaining member and extending within said inverted portion and engaging an internal surface of said inverted portion.

Any one or more of the following features, designs and configurations can be incorporated in the presently disclosed subject matter according to the seventh and eighth aspects, independently or in combination thereof.

The sleeve supporting member is configured to preserve the shape of said inverted portion at the engagement area therebetween.

The sleeve supporting member can be pivotally connected to the retaining member.

The sleeve supporting member can have a cylindrical shape.

The sleeve supporting member can be connected to the retaining member via an extension member. The sleeve supporting member can be pivotally connected to the extension member.

BRIEF DESCRIPTION OF THE DRAWINGS

In order to better understand the subject matter that is disclosed herein and to exemplify how it may be carried out in practice, embodiments will now be described, by way of non-limiting examples only, with reference to the accompanying drawings, in which:

FIG. 3 is a top view of the device of FIG. 1B, in its elongated state along a curved path.

DETAILED DESCRIPTION OF EMBODIMENTS

Figure 1A:
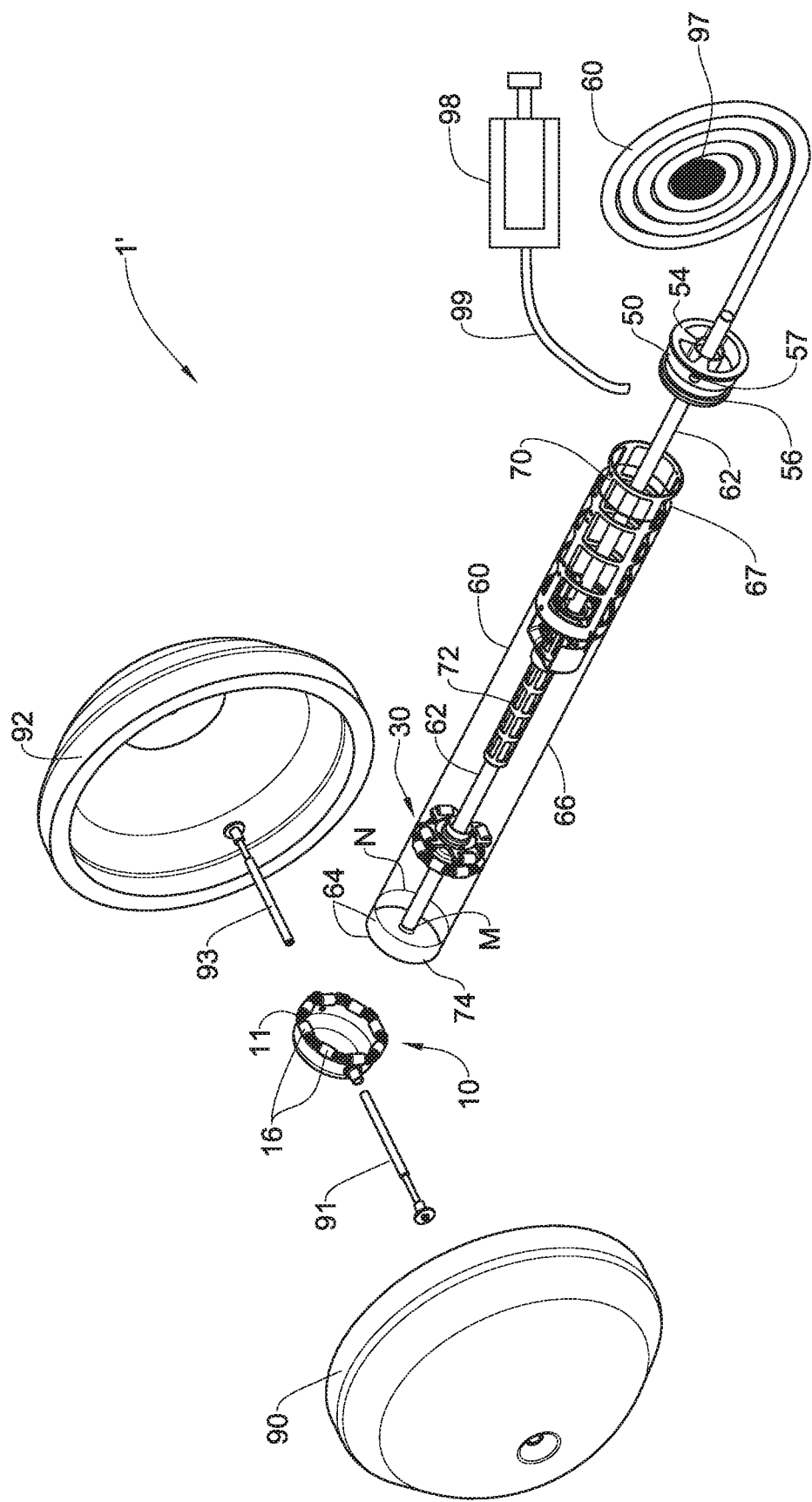
FIG. 1A is an exploded isometric view of a device according to one example of the presently disclosed subject matter, constituting a system for advancing an article along a path.

Attention is directed to FIGS. 1A-G and 2A-2F in which a system 1' (FIG. 1A) and a device 1 (FIG. 1B) for advancing an article along a path are shown, in accordance with one example of the presently disclosed subject matter. The device 1 constitutes an assembled form of the system 1', and therefore, although explanations below are made with respect to the device 1, they are also relevant for the system 1'.

The device 1 comprises a head member 10 having a retaining member 30, a dispatching member 50, an eversion sleeve 60, and a pumping mechanism in the form of a pump 98. The device 1 can optionally comprise an operational unit 100 (FIG. 3) which can be mounted to the head member 10 when needed. The operational unit 100 can include one or more of the following: a video camera, a stills camera, an imaging system, sensing system, a treatment system, a working tool, and a communication system.

Figure 1B:
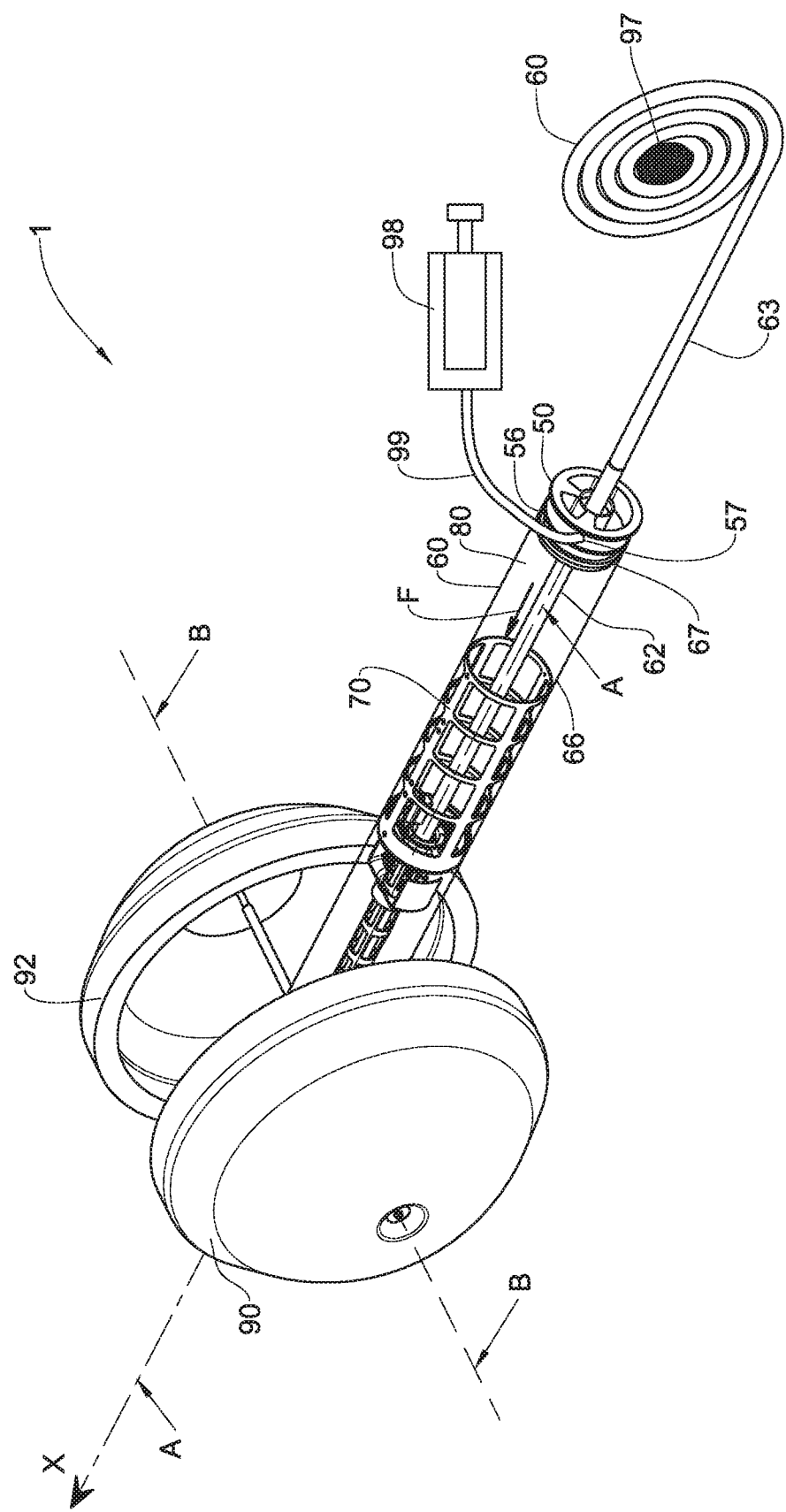
FIG. 1B is a rear isometric view of the device of FIG. 1A, in its assembled form.
Figure 1C:
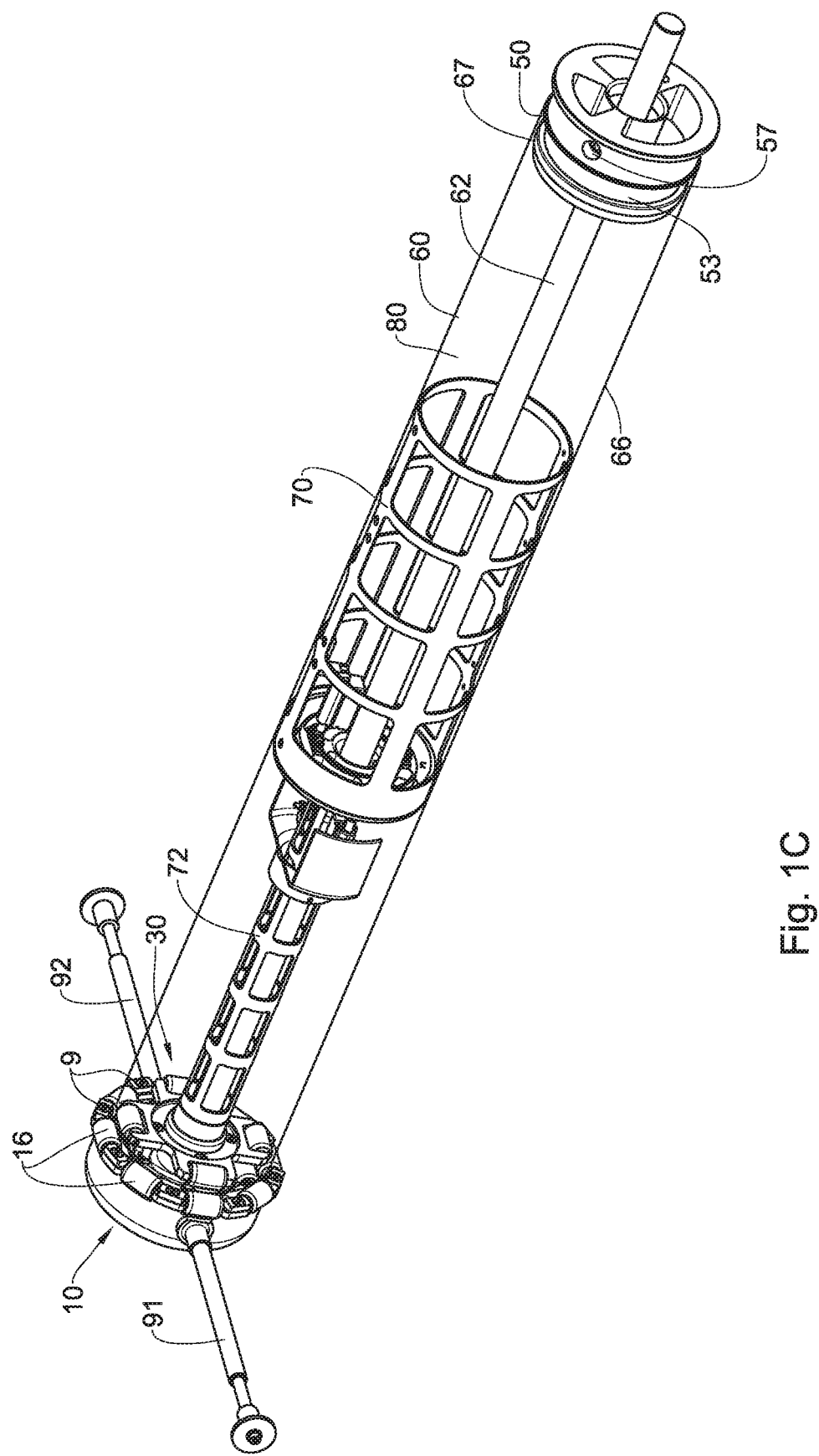
FIG. 1C is the device of FIG. 1B, shown without its wheels.
Figure 1D:
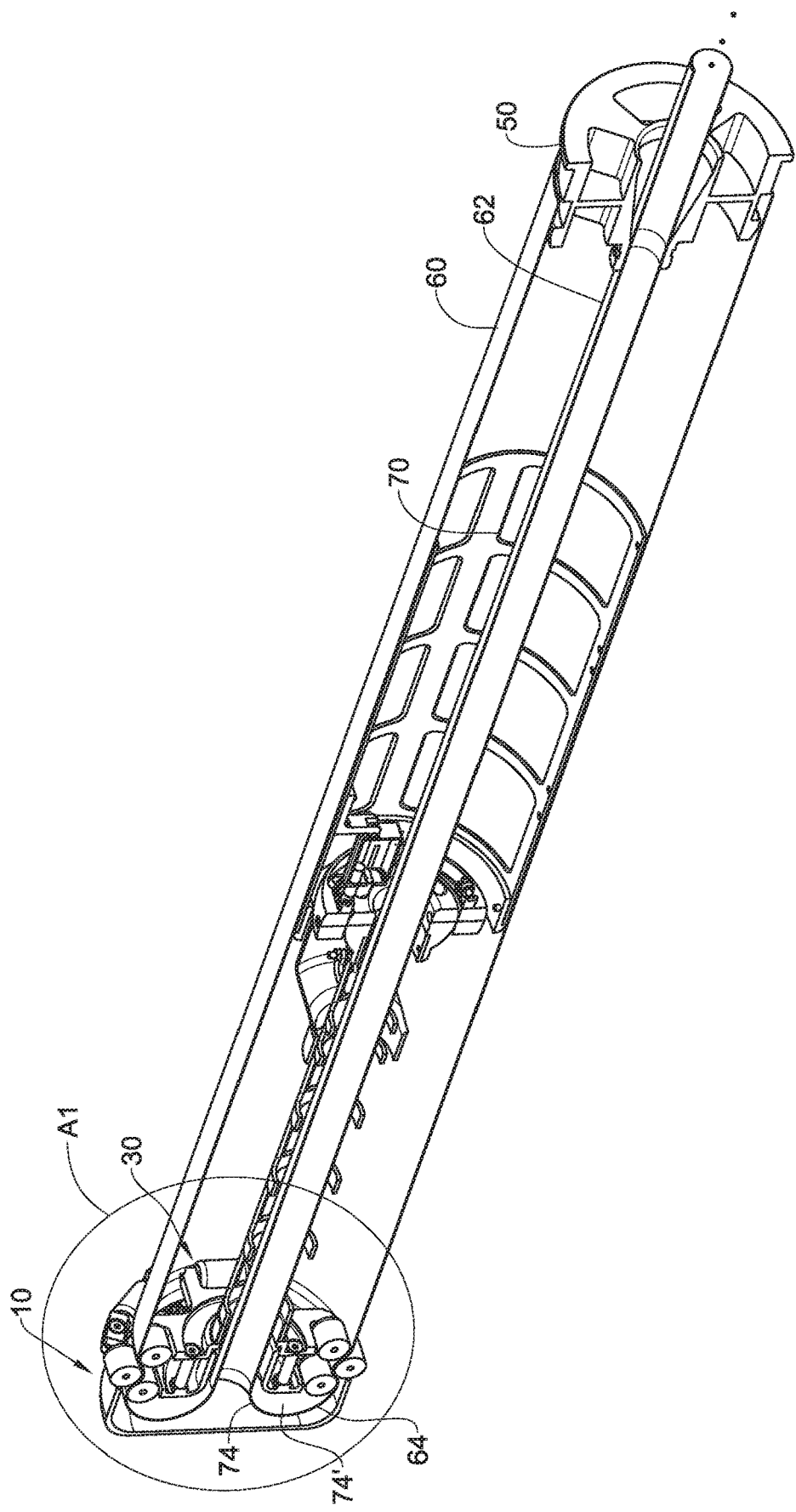
FIG. 1D is a cross-sectional view taken along line A-A of the device of FIG. 1B, shown without it wheel.
Figure 1E:
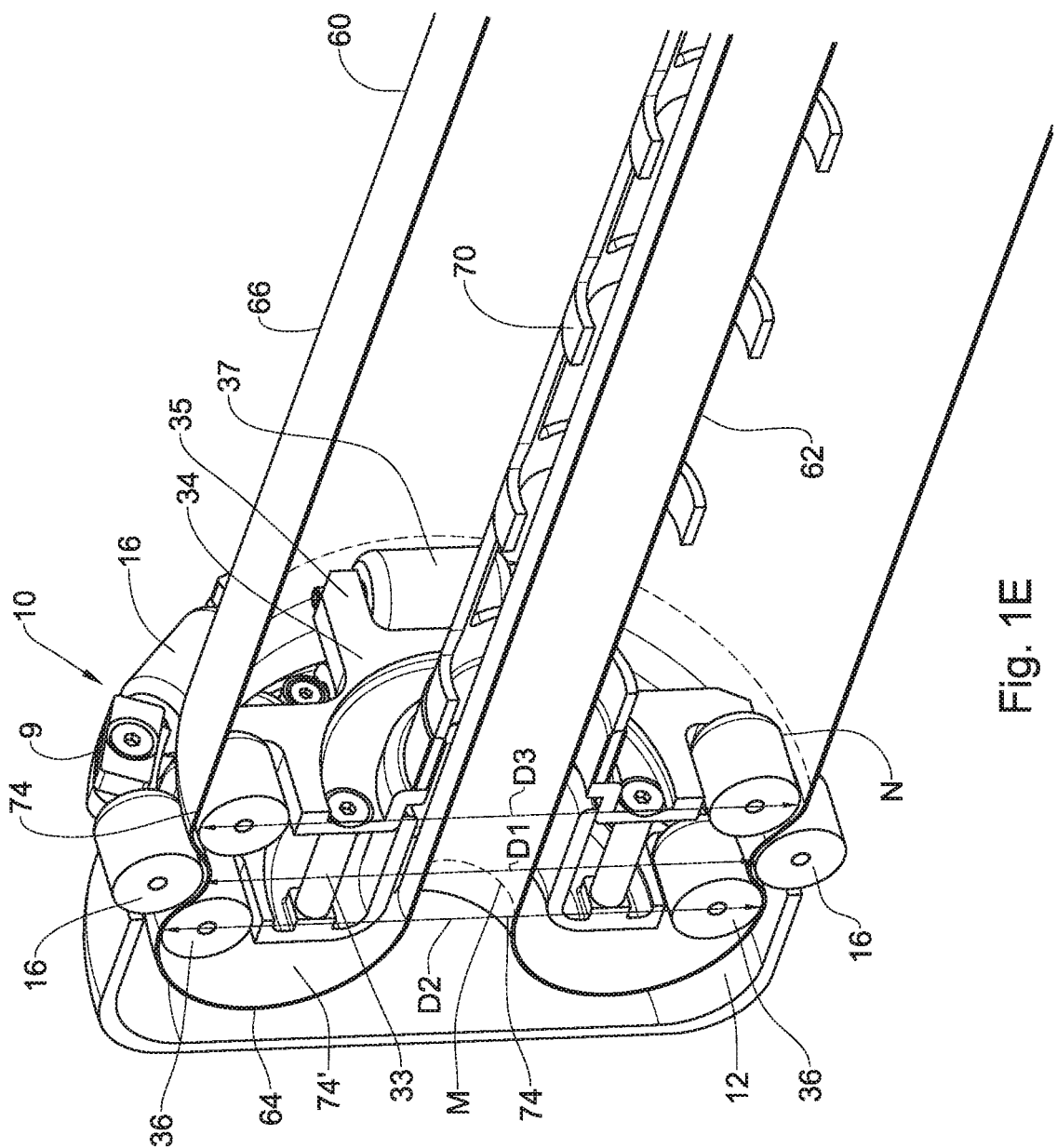
FIG. 1E is an enlarged view of portion A1 of FIG. 1D.
Figure 1F:
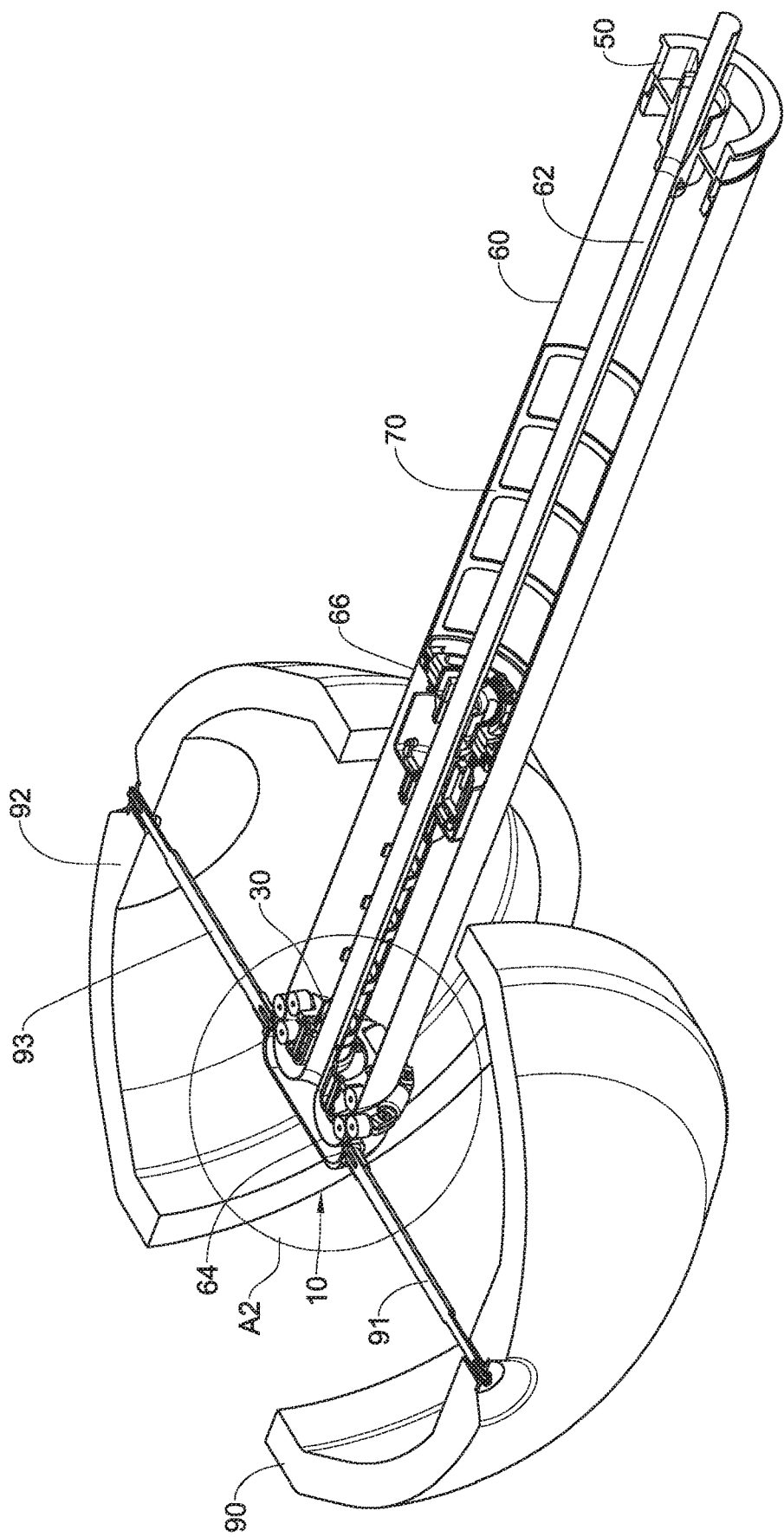
FIG. 1F is a cross-sectional view taken along line B-B of the device of FIG. 1B.
Figure 1G:
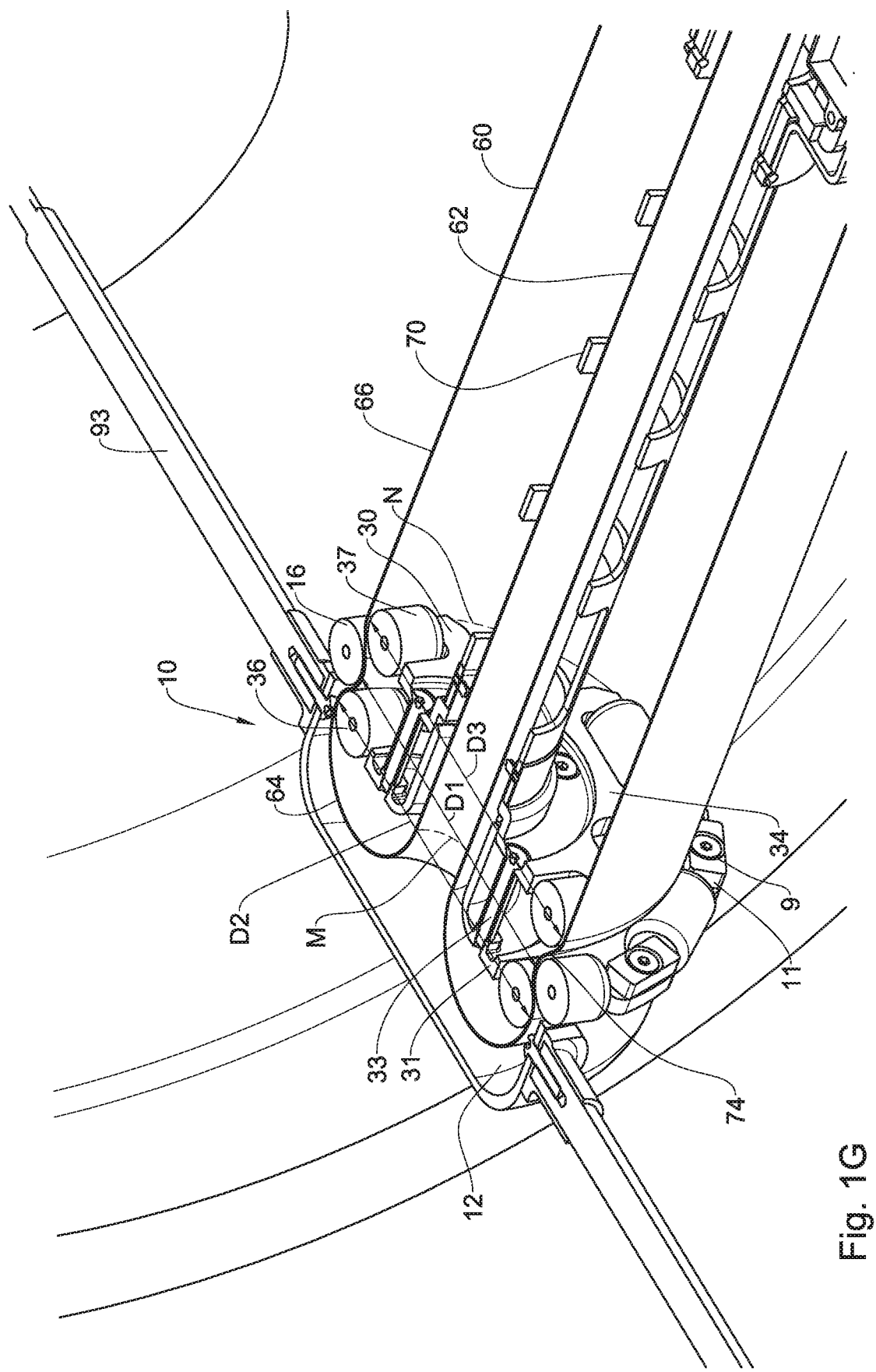
FIG. 1G is an enlarged view of portion A2 of FIG. 1F.
Figure 2A:
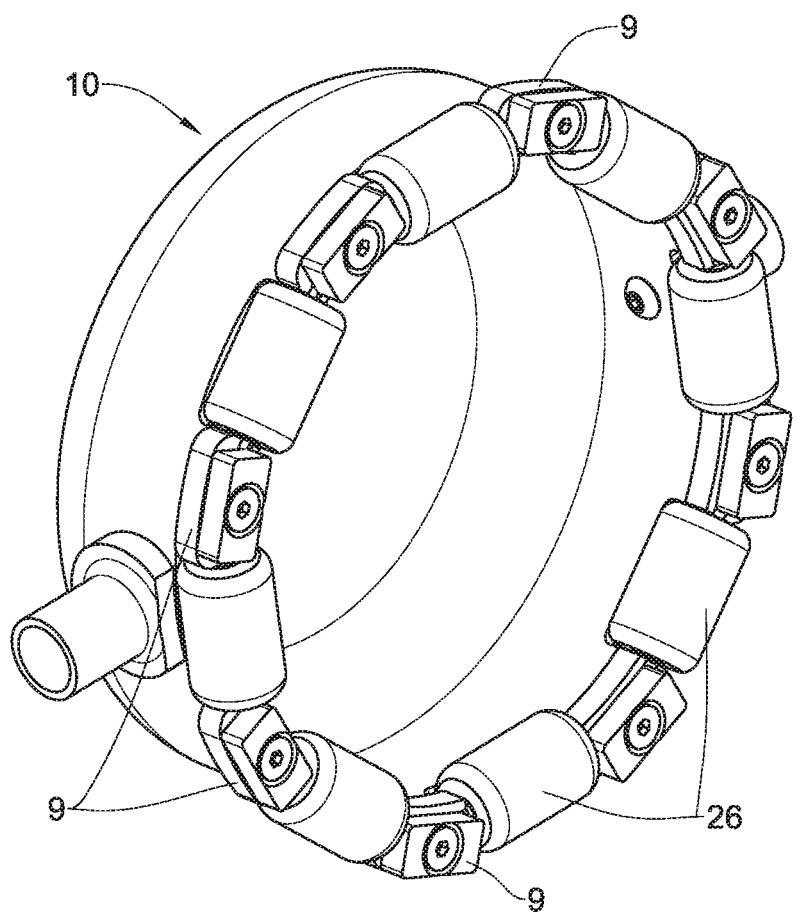
FIG. 2A is an enlarged view the head member of FIG. 1A, shown without its retaining member.
Figure 2B:
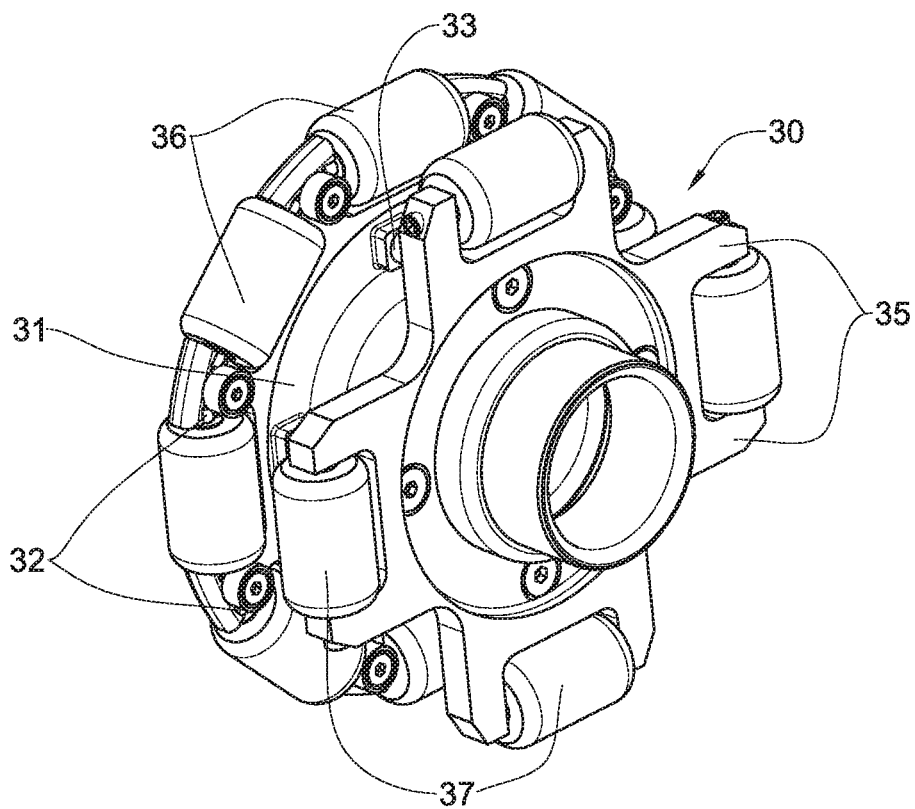
FIG. 2B is an enlarged view of the retaining member of the head member of FIG. 1A.
Figure 2C:
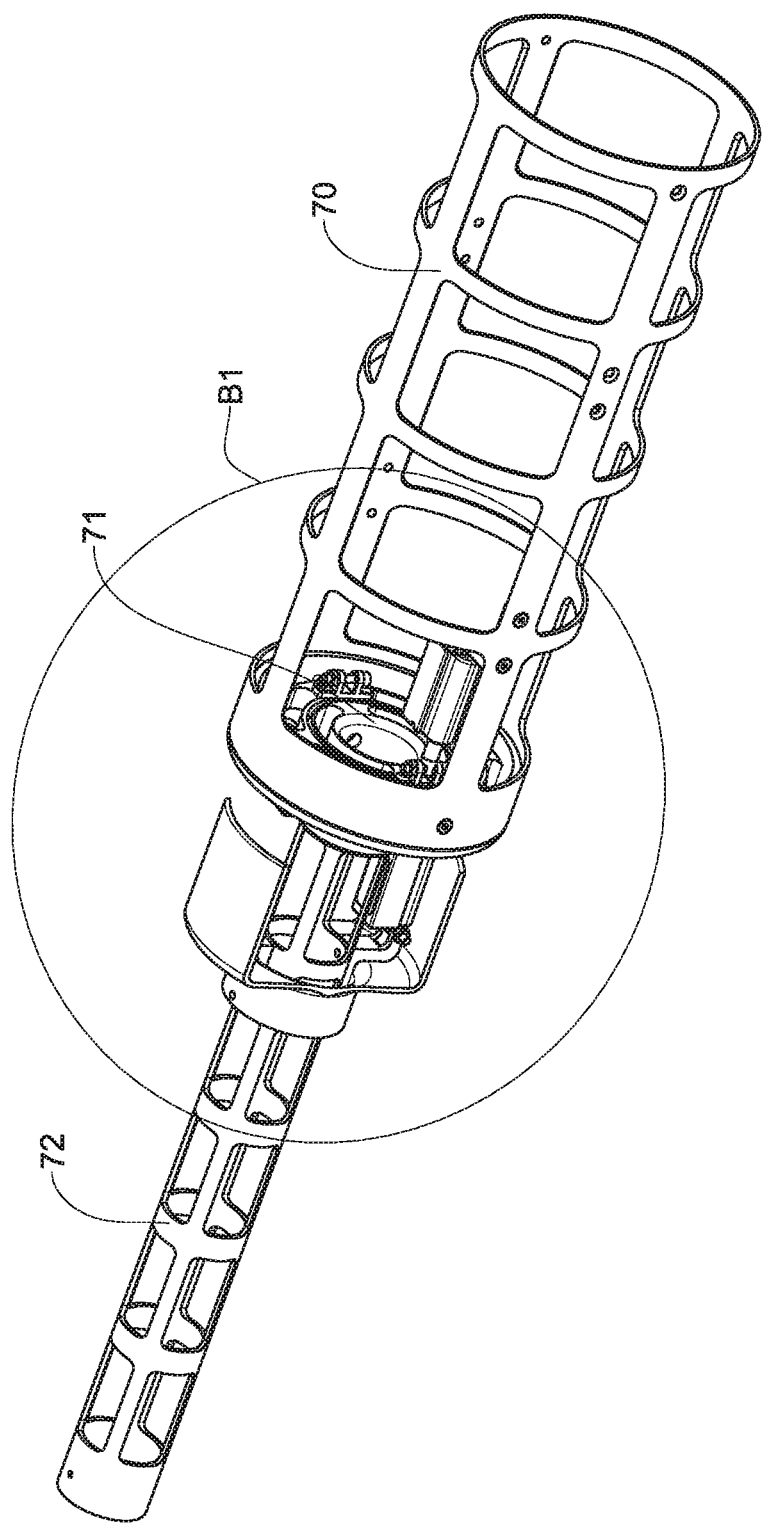
FIG. 2C is an enlarged view of the sleeve supporting member of FIG. 1A.
Figure 2D:
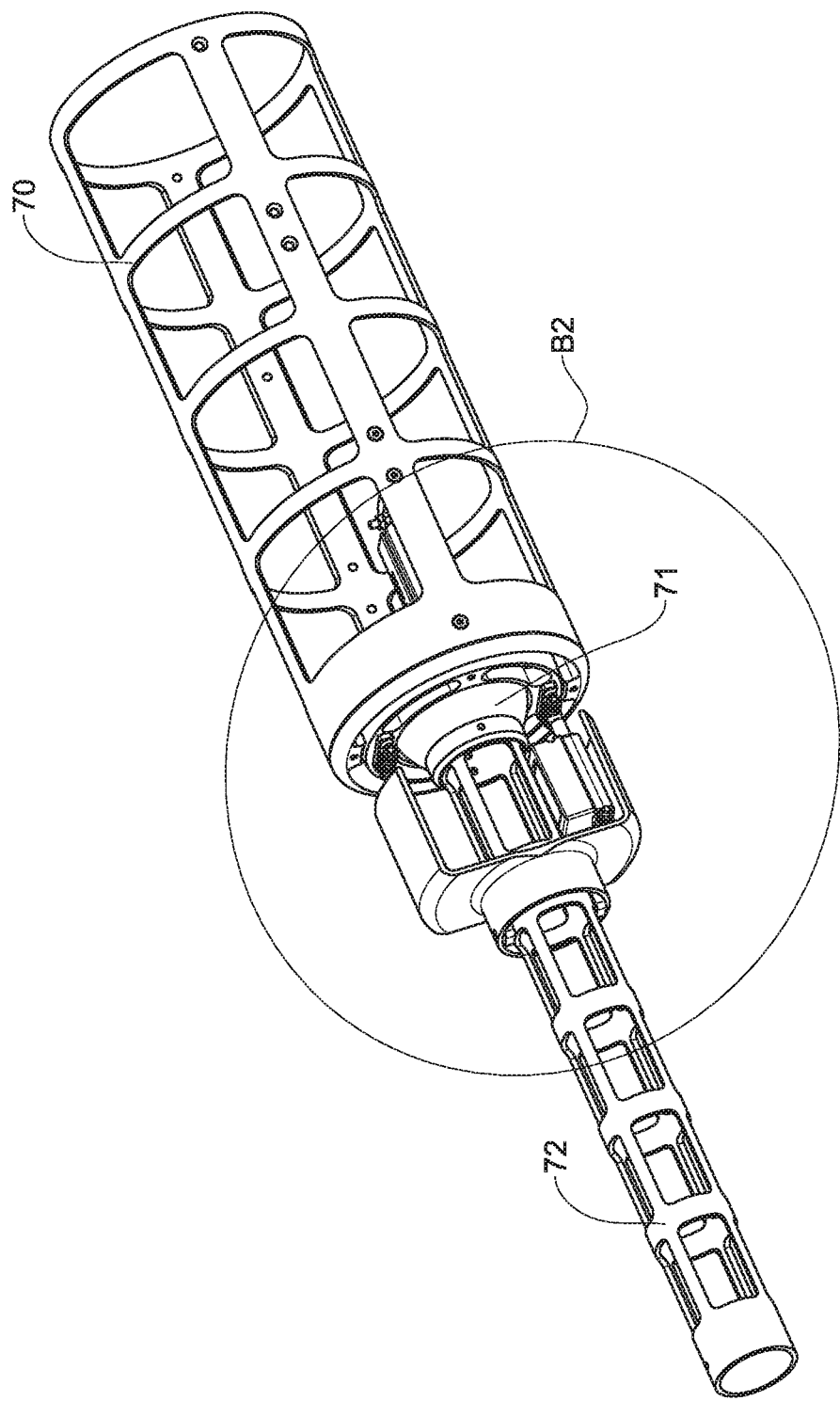
FIG. 2D is a front isometric view of the sleeve supporting member of FIG. 2C.
Figure 2E:
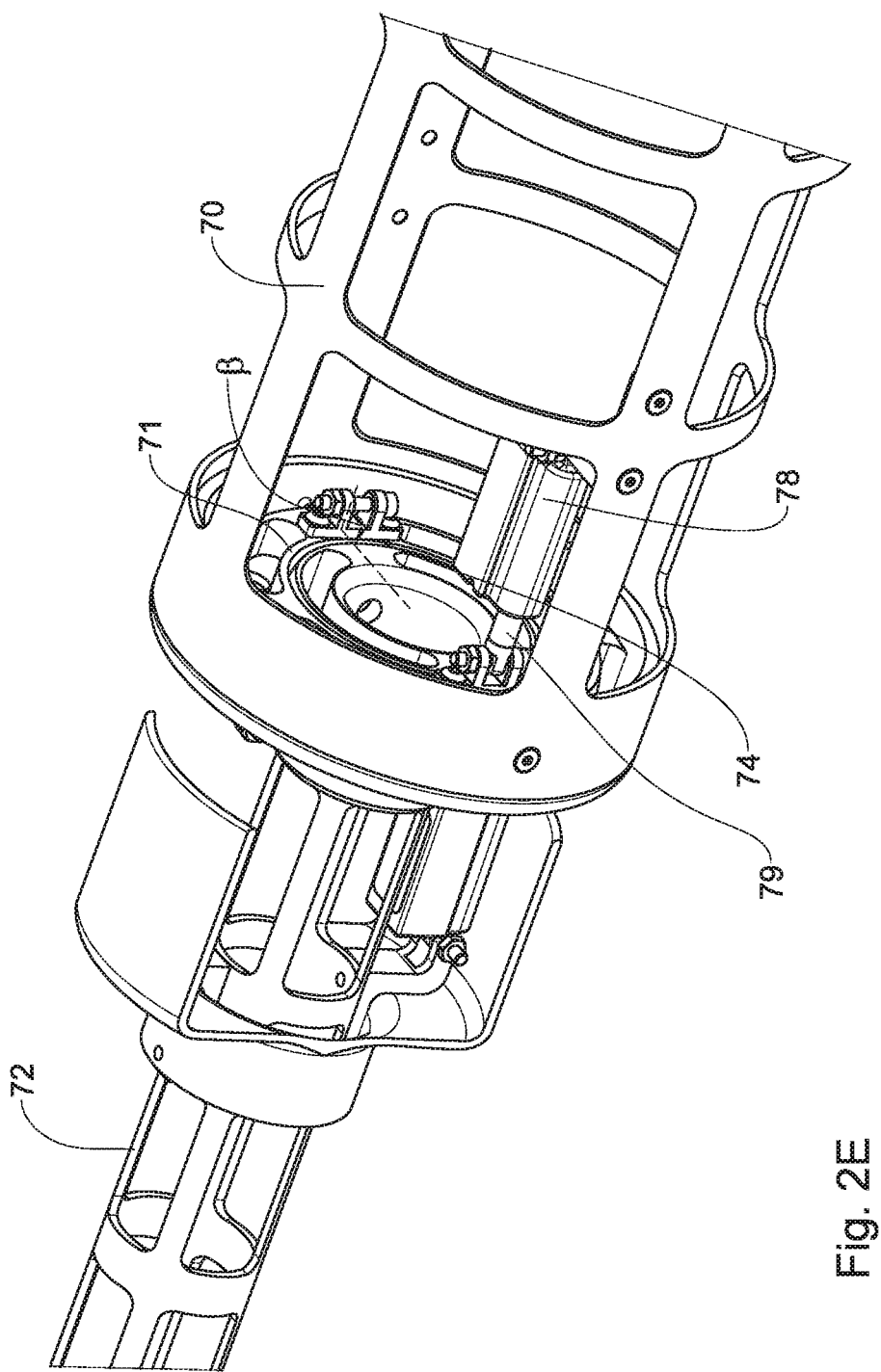
FIG. 2E is an enlarged view of portion B1 of FIG. 2C.
Figure 2F:
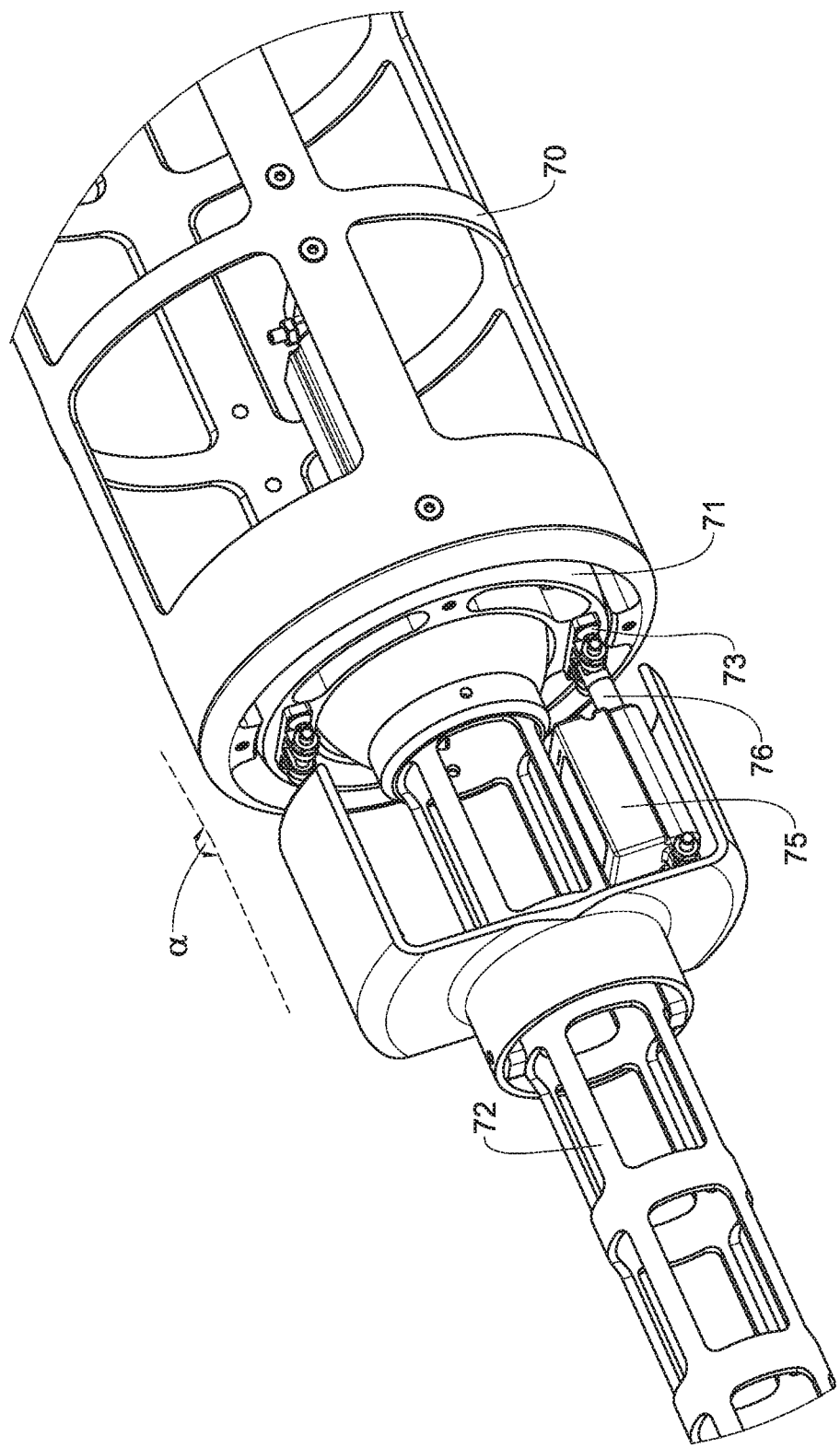
FIG. 2F is an enlarged view of portion B2 of FIG. 2D.

As shown in FIGS. 1A and 1B, the eversion sleeve 60 is an elongate sleeve wound about a take-up reel 97. The eversion sleeve 60 is shown in FIGS. 1A-G with its front end turned inside out, thereby forming three main portions: a non-inverted portion 62, an everting portion 64 and an inverted portion 66 which is turned at an angle of 180° with respect to the non-inverted portion 62. As shown in FIGS. 1A, 1E and 1G, the everting portion 64 is defined as a portion of the eversion sleeve 60 which extends between imaginary circles M and N of the sleeve. It should be indicated that the location of the everting portion 64, and respectively the length of the non-inverted portion 62 and the inverted portion 66 is dynamic, and depends on the extent of eversion of the eversion sleeve 60, as described below.

The eversion sleeve 60 is made of a fluid-tight material, for example, nylon. When being put under pressure, the eversion sleeve 60 is resilient and flexible, thereby allowing advancement of the head member 10 along a curved path, as explained below with reference to FIG. 3. Although the everting portion 64 of FIG. 1A is shown in its non-deformed state, when the device 1 is assembled, and particularly, when the head member 10 and its retaining member 30 are mounted to the everting portion 64, the shape of the everting portion is changed in accordance with the structure of the head member 10 and the retaining member 30 (as shown in FIGS. 1D-G).

As explained in a detailed manner below, in operation of the device 1, introduction of a propelling fluid into the interior of the device 1 causes the eversion sleeve 60 to be continuously everted while increasing the length of the inverted portion 66 and decreasing the length of the non-inverted portion 62. This eversion is followed by displacement of the head member 10 and its retaining member 30 with respect to the eversion sleeve 60, which results in movement of the head member 10 along an elongation X-axis (shown in FIG. 1B) extending along the length of the device 1.

The dispatching member 50 includes an annular housing 54 with a nozzle 53 disposed at its center for allowing the non-inverted portion 62 to pass therethorugh. The housing 54 is configured with a perimetric rim 56. As shown in FIGS. 1B and 1C, a sleeve end 67 of the inverted portion 66 is sealingly fixed to the perimetric rim 56. The housing 54 further has an inlet 57 for interfacing with the pump 98 for fluidly communicating therebetween. The non-inverted portion 62 is extending from the everting portion 64 towards the dispatching member 50, and from there to the take-up reel 97. The everting portion 64 is configured with an external surface 74 and an internal surface 74'.

The head member 10 is provided with an internal portion 12 and with eight first revolving elements 16 in the form of rollers which are equally spaced from each other at a head member end 11. Each one of the first revolving elements 16 is held between two holding members 9 and pivotally rotatable with respect to the holding members 9. The first revolving elements 16 are engaging the external surface 74 of the everting portion 64. The first revolving elements 16 are configured for revolving upon displacement of the everting portion 64 thereon with respect to the head member 10.

The retaining member 30 is used for retaining the head member 10 to the eversion sleeve 60 by engaging the internal surface 74' of the everting portion 64 on which the force of the propelling fluid is to be exerted, and applying an outwardly pressing force thereon, thereby retaining the everting portion 64 in proximity to the first revolving members 16 while allowing the everting portion 64 for displacing with respect to the revolving members 16.

In particular, the retaining member 30 is configured as a first retaining sub-member 31 and a second retaining sub-member 34 spaced from each other and connected to each other by connectors 33. The first retaining sub-member 31 has eight second revolving members 36 in the form of rollers which are equally spaced from each other, and the second retaining sub-member 34 has four second revolving members 37 in the form of rollers which are also equally spaced from each other. Each one of the second revolving members 36 is held and rotatable between two holding members 32 of the first retaining sub-member 31, and each one of the second revolving members 37 is held and rotatable between two holding members 35 of the second retaining sub-member 34.

The retaining of the head member 10 to the eversion sleeve 60 is performed by positioning the retaining member 30 from the side of the internal surface 74', so that the everting portion 64 is disposed between the retaining member 30 and the head member 10. In this position, the retaining member 30 applies an outwardly pressing force on the internal surface 74', thereby retaining the everting portion 64 in proximity to the internal portion 12 while allowing the everting portion 64 to displace with respect to the internal portion 12.

The retaining member 30 is disposed within the head member 10 with the everting portion 64 therebetween, while the first revolving members 16 are engaging the external surface 74, and the second revolving members 36 and 37 are engaging the internal surface 74'. The first revolving members 16 are disposed between the second revolving members 36 and 37 at the space between the first retaining sub-member 31 and the second retaining sub-member 34.

As shown in FIGS. 1E and 1G, the first revolving elements 16 are forming a narrow portion having a first cross-sectional diameter D1 taken perpendicularly to its length along the X-axis between innermost ends of the first revolving elements 16. The second revolving elements 36 are forming a second cross-sectional diameter D2 taken perpendicularly to the X-axis between outmost ends of the second revolving elements 36, and the second revolving elements 37 are forming a third cross-sectional diameter D3 taken perpendicularly to the X-axis between outmost ends of the second revolving elements 36. The first diameter D1 is smaller than the second diameter D2 and the third diameter D3. These relationships between these diameters allows retaining the retaining member 30 with respect to the head member 10. The second revolving elements 36 are disposed at a wide portion of the internal portion.

As best seen in FIGS. 1B and 1C, a fluid-tight sealable space 80 is formed within the device 1 between the non-inverted portion 62 and the inverted portion 66. The space 80 is in fluid communication with the pump 98 via a hose 99 which is connected to the inlet 57. The space 80 is sealed from the surroundings of the device 1 and is configured for receiving a propelling pressurized fluid in the form of air from the pump 98. The pump 98 can be manually or electrically operated.

Introduction of air into the space 80 increases the length of the inverted portion 66 while it remains stationary, thereby advancing the head member 10 along the X-axis by rolling the head member 10 with respect to the eversion sleeve 60 during rotation of the first and the second revolving members 16, 36 and 37.

As a result of introduction of a predetermined amount of air into the space 80, a pressure gradient is generated within the space 80 with respect to the surroundings of the device 1. Due to a limited resilience of the eversion sleeve 60 in the radial direction, the pressure of the air within the space 80 generates a force F (shown in FIG. 1B) directed generally along the X-axis. The force F is exerted on the everting portion 64 straightly and via the retaining member 30. Exertion of the force F applies a pulling force on the non-inverted portion 62 in the direction of the X-axis, gradually advancing a segment of the non-inverted portion 62 towards the head member 10 with respective rotation of the take-up reel 97. This segment has a length L (not shown). As a result of the pulling force applied thereon, the segment of the non-inverted portion 62 displaces between the head member 10 and the retaining member 30 while the first and the second revolving members 16, 36 and 37 are revolving, gradually advancing a segment of the everting portion 64 into the inverted portion 66. This results in increasing the length of the inverted portion 66 by a length of L/2 and advancing the head member in the X-axis direction to a distance of L/2. In other words, the exertion of the force F causes eversion of a segment of the eversion sleeve 60 having the length L, which results in advancement of the head member 10 along a distance of L/2. Therefore, during introduction of air into the space 80, the speed of advancement of the non-inverted portion 62 is twice than the speed of advancement of the head member 10.

The head member 10 is made of a rigid material that preserves its shape also when the pressure of air within the space 80 drops, for example, when the head member 10 was advanced to a particular location along the path, and the pump 98 was disconnected from the device 1. This ability of the head member 10 to preserve its shape allows it to perform its designated function (e.g., measuring, sensing, optically inspecting, etc.) at any location along the path also when there is a pressure drop within the space 80.

An interior of the internal portion 62 defines an elongate lumen 63 (shown in FIG. 1B) allowing electrically or mechanically communicating therethrough between an exterior of the device at the surroundings of the dispatching member and the head member 10 and its surroundings. The lumen 63 can allow introducing therethrough into the location of the head member along the path different objects (e.g., endoscopes, measuring instruments, sensors, working tools), cables (e.g., electric cables, Bowden cables, fibers), or elongate elements.

The device 1 is further configured with a cylindrical sleeve supporting member 70 connected to the retaining member 30 via an extension member 72. The sleeve supporting member 70 is extending within the inverted portion 66 and engaging an internal surface thereof. The sleeve supporting member 70 is sized so as to preserve the shape of the inverted portion 66 at the engagement area with the inverted portion 66 and to provide stability thereto.

The device 1 is further configured with a steering mechanism mounted on the head member 10 for directing the head member 10 during its advancement along the path.

The steering mechanism is structured of a pair of first and second wheels 90 and 92 connected to an exterior of the head member 10 at two opposite sides thereof, and a controlling mechanism for controlling the direction of the wheels 90 and 92. The controlling mechanism is constituted by the sleeve supporting member 70, the extension member 72, and further elements, as detailed below, responsible for directing movement of the head member 10 with respect to the X-axis of the eversion sleeve 60.

The first wheel 90 is connected to the head member 10 via a first axle 91, and the second wheel 92 is connected to the head member 10 via a second axle 93. The first and the second axles extend from an external surface of the head member 10, and allow pivotal rotation of the first and second wheels 90 and 92 with respect to the head member, when the head member 10 is displaced along the path and the wheels 90 and 92 roll over the surface of the path.

Detailed explanations are now provided with respect to the sleeve supporting member 70 and the extension member 72. The sleeve supporting member 70 is configured with a sub-supporting member 71 disposed at its end in proximity to the extension member 72. In particular, the sub-supporting member 71 pivotally connected at one end 73 thereof to the extension member 72, and at another end 74 thereof pivotally connected to the sleeve supporting member 70. The pivotal connection of the sub-supporting member 71 to the extension member 72 and to the sleeve supporting member 70 constitute an angle-regulating mechanism configured for regulating the angle between the retaining member 30 and the sleeve supporting member 70 on two perpendicular planes. The extension member 72, the sleeve supporting member 70 and the sub-supporting member 71 each have a central opening allowing the non-inverted portion 63 to pass therethrough.

The angle-regulating mechanism has a first hydraulic cylinder 75 pivotally interconnecting the end 73 to the extension member 72. The first hydraulic cylinder 75 has a first piston 76 linearly movable with respect to a first housing 77 of the first hydraulic cylinder 75. Linear movement of the first piston 76 changes a first angle $\alpha$ (shown in FIG. 2F) between the extension member 72 and the sub-supporting member 71. The angle $\alpha$ shown in FIG. 2F as an angle of 180°, which can be changed to an angle greater or smaller than 180° as a result of the operation of the first hydraulic cylinder 75.

The angle-regulating mechanism further has a second hydraulic cylinder 78 interconnecting the sub-supporting member 71 to the sleeve supporting member 70. The second hydraulic cylinder 78 has a second piston 79 linearly movable with respect to a second housing 80 of the second hydraulic cylinder 78. Linear movement of the second piston 79 changes a second angle $\beta$ (shown in FIG. 2E) between the sleeve supporting member 70 and the sub-supporting member 71. The angle $\beta$ shown in FIG. 2E as an angle of 90°, which can be changed to an angle greater or smaller than 90° as a result of the operation of the second hydraulic cylinder 78. The angles $\alpha$ and $\beta$ are disposed at two perpendicular planes, allowing forming any angle between the head member 10 and the sleeve supporting member 70, thereby changing the direction of the head member 10 along the path.

Reference is now made to FIG. 3 in which the device 1 is shown within a curved path 200. As mentioned above, the eversion sleeve 60 is made of a resilient and/or flexible material that allows advancing the inverted portion 66 of the eversion sleeve 60 with the head member 10 mounted thereto along the curved structures. For example, when the head member 10 is advanced along the path 200, and reaches the wall of the path 200 at a turning point 202, further advancement of the head member 10 will cause the inverted portion 66 to bend, thereby following the shape and the structure of the path 200. In addition, in order to facilitate this bending, the angle-regulating mechanism is used for operating the first hydraulic cylinder 75 and changing the angle $\alpha$ to be greater than 180°, It should be indicated that the head member 10 can also be advanced backwardly within path 200, for example, after finishing its intended operation. This can be done by reducing the pressure within the space 80, thereby allowing gradually pulling the non-inverted portion 62 in the opposite direction, resulting in decrease of the length of the inverted portion 62 and respective backward movement of the head member 10.

Although the eversion sleeve 60 has a finite length, its length can be manually or automatically increased by sealingly connecting thereto an additional eversion sleeve by techniques known in the art (e.g., heat welding). This can allow advancing the head member 10 along a path which is extremely long, even more than it was known to the operator prior to the introduction of the head member into the path.

The invention claimed is:

1. A system for advancing an article along a path, comprising:
    a head member;
    a dispatching member; and
    an eversion sleeve configured with an inverted portion having a sleeve end configured to be fixed to the dispatching member, an everting portion configured for articulating to the head member and a non-inverted portion configured to extend from the everting portion towards the dispatching member, at least partially within the inverted portion; said non-inverted portion and said inverted portion are configured to form a fluid receiving space therebetween for receiving a propelling fluid for exerting force on the everting portion, thereby advancing a segment of the non-inverted portion towards the head member, causing the segment of the non-inverted portion to displace with respect to the head member, advancing a respective segment of the everting portion into the inverted portion, thereby everting said eversion sleeve inside out and advancing the head member along the path;
    wherein said head member is configured with one or more revolving elements configured for engaging said everting portion and for revolving upon displacement of the everting portion thereon with respect to the head member.

2. The system according to claim 1, wherein the head member is configured with an internal portion for retaining the everting portion and facilitating the everting portion to advance with respect to the head member.

3. The system according to claim 2, wherein the one or more revolving elements comprise one or more first revolving elements configured with said internal portion for engaging an external surface of said everting portion.

4. The system according to claim 3, wherein the one or more first revolving elements are equally spaced from each other.

5. The system according to claim 2, wherein the internal portion of the head member is configured with at least one narrow portion having a first cross-sectional diameter D1 taken perpendicularly to a length of the internal portion of the head member and at least one wide portion having a second cross-sectional diameter D2 taken perpendicularly to the length of the internal portion of the head member, which is greater than D1; and wherein said at least one narrow portion is configured to engage an external surface of the everting portion and prevent axial displacement of the head member with respect to the everting portion, while allowing the everting portion to displace with respect to the internal portion.

6. The system according to claim 5, wherein the one or more revolving elements comprise one or more first revolving elements configured with said internal portion for engaging the external surface of said everting portion, and wherein the one or more first revolving elements are disposed at said narrow portion.

7. The system according to claim 6, wherein said one or more first revolving elements define the first cross-sectional diameter D1.

8. The system according to claim 5, wherein the at least one narrow portion is formed in the head member as a circumferential groove.

9. The system according to claim 5, wherein said at least one narrow portion is disposed closer to the inverted portion than the at least one wide portion.

10. The system according to claim 5, wherein said at least one narrow portion is disposed between two of said at least one wide portions.

11. The system according to claim 2, wherein said head member further comprises a retaining member configured for engaging an internal surface of the everting portion on which the force of the propelling fluid is to be exerted, and applying an outwardly pressing force thereon, thereby retaining the everting portion while allowing the everting portion for displacing with respect to the internal portion for retaining the everting portion.

12. The system according to claim 11, wherein said one or more revolving elements comprise one or more second revolving elements configured with the retaining member for engaging the internal surface of the everting portion and for revolving upon displacement of the everting portion thereon with respect to the head member.

13. The system according to claim 12, wherein the one or more revolving elements comprise one or more first revolving elements configured with said internal portion for engaging an external surface of said everting portion, and wherein one or more of the first revolving elements are disposed in proximity to one or more of the second revolving elements so that the everting portion is disposed therebetween.

14. The system according to claim 11, wherein said retaining member is configured as a first retaining sub-member and a second retaining sub-member disposed consecutively along a length of the head member.

15. The system according to claim 11, wherein said retaining member has a central opening for allowing the non-inverted portion to pass therethrough.

16. A method for assembling a system for advancing an article along a path, the system comprising: a head member configured with one or more revolving elements configured for engaging said an everting portion and for revolving upon displacement of the everting portion thereon with respect to the head member; a dispatching member having a nozzle; and an eversion sleeve; the method comprising:

(i) introducing a part of said eversion sleeve via said nozzle;

(ii) everting the eversion sleeve inside out, thereby forming an inverted portion having a sleeve end, the everting portion and a non-inverted portion extending from the everting portion towards the dispatching member, at least partially within the inverted portion; and (iii) mounting said everting portion to said head member so that said one or more revolving elements are engaging an external surface of said everting portion to facilitate displacement of the everting portion with respect to the head member; and (iv) sealingly fixing said sleeve end to said dispatching member, thereby forming a space therebetween for receiving a propelling fluid for exerting force on the everting portion.

17. The method according to claim 16, further comprising steps of: introducing said part of said eversion sleeve via a retaining member, which is performed between steps (i) and (ii); and locating the retaining member at an internal surface of the everting portion for applying an outwardly pressing force thereon, which is performed between steps (iii) and (iv).

18. The method according to claim 17, wherein said step (iv) further includes a step of locating the retaining member within a wide portion of the head member.

19. A method for using a device for advancing an article along a path, comprising:

(i) providing the device, comprising: a head member; a dispatching member; an eversion sleeve configured with an inverted portion having a sleeve end fixed to the dispatching member, an everting portion articulated to the head member and a non-inverted portion extending from the everting portion towards the dispatching member, at least partially within the inverted portion; and a space formed between said non-inverted portion and said inverted portion; said head member being configured with one or more revolving elements configured for engaging said everting portion and for revolving upon displacement of the everting portion thereon with respect to the head member;

(ii) locating said device at a particular location at the path with the head member facing towards an advancement direction along the path; and (iii) introducing a propelling fluid into the space for exerting force on the everting portion, thereby advancing a segment of the non-inverted portion towards the head member causing the segment of the non-inverted portion to displace with respect to the head member while the one or more revolving elements are revolving and advancing a respective segment of the everting portion into the inverted portion, thereby everting said eversion sleeve inside out and advancing the head member along the advancement direction.

20. The method according to claim 19, further comprising steps of: providing the device with a steering mechanism having a body member connected to a front end of the head member; and operating the steering mechanism for directing the advancement direction of the head member.

* * * * *